United States Patent [19]

Nakao et al.

[11] Patent Number: 5,723,465

[45] Date of Patent: Mar. 3, 1998

[54] INHIBITORS FOR CELL ADHESION AND CELLULAR INFILTRATION

[75] Inventors: Hiroshi Nakao, Tsuchiura; Michihisa Umetani, Tokyo; Makoto Suda, Tsukuba; Takao Nagoya, Tsuchiura, all of Japan

[73] Assignee: Kowa Co., Ltd., Nagoya, Japan

[21] Appl. No.: 746,811

[22] Filed: Nov. 18, 1996

[30] Foreign Application Priority Data

Nov. 20, 1995 [JP] Japan .................. 7-301526

[51] Int. Cl.$^6$ .................. A61K 31/495; A61K 31/55
[52] U.S. Cl. .................. 514/255; 514/218
[58] Field of Search .................. 514/255, 218

[56] References Cited

U.S. PATENT DOCUMENTS 5,389,630  2/1995  Sato et al. .................. 514/218

OTHER PUBLICATIONS

Goodman et al. "The Pharmacological Basis of Therapeutics", 6th ed. pp. 1249–1255.

Primary Examiner—Raymond Henley, III

Attorney, Agent, or Firm—Oblon, Spivak, McClelland, Maier & Neustadt, P.C.

[57] ABSTRACT

The present invention is directed to a cell adhesion inhibitory agent, cellular infiltration inhibitory agent, antiallergic agent, antiasthmatic agent, and antiphlogistic, which contains a compound of the following formula (1):

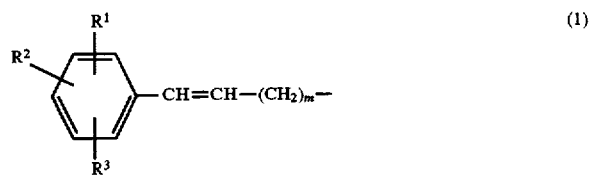

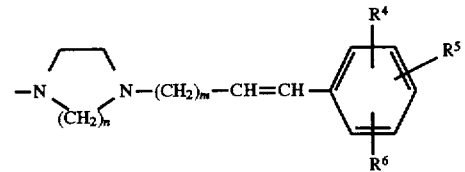

wherein each of $R^1$ through $R^6$ represents H, a halogen atom, a hydroxyl group, a lower alkyl group, or a lower alkoxy group, m represents a number of 1 from 3 inclusive, and n represents 2 or 3.

2 Claims, No Drawings

INHIBITORS FOR CELL ADHESION AND CELLULAR INFILTRATION

BACKGROUND OF THE INVENTION

1) Field of the Invention

The present invention relates to pharmaceuticals containing as the active ingredient a diamine compound or a salt thereof, the compound exhibiting cell adhesion inhibitory action and cellular infiltration inhibitory action and thus being useful as an antiasthmatic agent, antiallergic agent, antirheumatic agent, antiarteriosclerotic agent, antiphlogistic, or anticancer agent.

2) Background Art

In various types of inflammation, infiltration of leukocytes and lymphocytes is observed in the inflamed site. For example, the trachea is infiltrated by eosinocytes in asthmatic patients (Ohashi et al., Allergy, 39, 1541–1549 (1990)); blood vessels are infiltrated by macrophages in arteriosclerosis (Ross R., Nature, 362, 801–809 (1993)); and the synovialis is infiltrated by different types of leukocytes in acute inflammatory sites, contact dermatitis, and in patients suffering articular rheumatism (Arend W. P. & Dayer J. M., Arthritis Rheum., 33, 305–315 (1990)).

Infiltration of leukocytes and lymphocytes is caused by cytokines, chemokines, lipids, and complements (Albelda S. M. et al., FASEB J., 8, 504–512 (1994)). Activated leukocytes in flowing blood interact with endothelial cells that are activated by cytokines such as IL-1 or TNFα, to thereby adhere to the endothelial cells. Such interaction is called rolling or tethering. The leukocytes then transmigrate through the endothelium to infiltrate the inflamed sites.

It has been reported that a variety of adhesive molecules such as selectin, integrin, members of the immunoglobulin family, and CD44 participate in the interaction between leukocytes and endothelial cells (Albelda S. M. et al., FASEB J., 4, 2868–2880 (1990)). Moreover, it has been reported that these adhesive molecules also participate in homing of lymphocytes (Shimizu Y., et al., Immunology Today, 13, 106–112 (1992)). In addition, it has been reported that these adhesive molecules also participate in adhesion to endothelial cells in metastatic cancers (Gorski A., Immunology Today, 15, 251–255 (1994)).

Thus, cell adhesion of leukocytes or cancer cells to endothelial cells is critical in infiltration of leukocytes into inflamed sites and in metastasis of cancers.

Accordingly, it is envisaged that a substance that inhibits such cell adhesion and cellular infiltration would serve as an effective pharmaceutical against pathological conditions or inflammations such as asthma, allergy, and rheumatism; as well as metastasis of cancers.

Until the present, there has never been reported such a substance exhibiting, through cell adhesion inhibitory mechanism and cellular infiltration inhibitory mechanism, excellent antiinflammatory action such as antiasthmatic action, antiallergic action, antirheumatic action, and antiarteriosclerotic action, as well as anticancer action.

In view of the foregoing, the present inventors conducted careful studies in an attempt to obtain a substance that inhibits cell adhesion and cellular infiltration, and found that the compound represented by the following formula (1) exhibits excellent cell adhesion inhibitory action and cellular infiltration inhibitory action, and is thus advantageously used as an antiallergic agent, antiasthmatic agent, antirheumatic agent, antiarteriosclerotic agent, antiphlogistic, etc. The present invention was accomplished based on this finding.

Therefore, an object of the present invention is to provide a pharmaceutical useful as an antiasthmatic agent, antiallergic agent, antirheumatic agent, antiarteriosclerotic agent, antiphlogistic, or cancerous metastasis inhibitory agent.

SUMMARY OF THE INVENTION

Accordingly, the present invention is to provide a cell adhesion inhibitory agent, cellular infiltration inhibitory agent, or a pharmaceutical for the treatment of pathological conditions attributed to cell adhesion or cellular infiltration (e.g., antiallergic agent, antiasthmatic agent, antirheumatic agent, antiarteriosclerotic agent, antiphlogistic, and cancerous metastasis inhibitory agent), containing as its active ingredient a compound of the following formula (1):

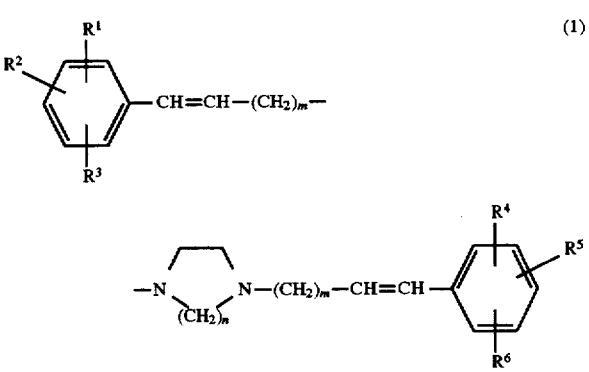

wherein each of $R^1$, $R^2$, $R^3$, $R^4$, $R^5$, and $R^6$, which are identical to or different from each other, represents a hydrogen atom, a halogen atom, a hydroxyl group, a lower alkyl group, or a lower alkoxy group, m represents a number of 1 from 3 inclusive, and n represents 2 or 3; an acid addition salt thereof; or a hydrate of the compound or the acid addition salt.

The present invention also provides use of the above-described compound of formula (1), an acid addition salt thereof, or a hydrate of the compound or the acid addition salt in the manufacture of a cell adhesion inhibitory agent and a cellular infiltration inhibitory agent as well as a preventive and therapeutic agent for pathological conditions attributed to cell adhesion or cellular infiltration.

The present invention also provides a method for inhibiting cell adhesion and cellular infiltration, characterized by interacting cells with the above-described compound of formula (1), an acid addition salt thereof, or a hydrate of the compound or the acid addition salt.

The present invention also provides a preventive and therapeutic method for pathological conditions attributed to cell adhesion or cellular infiltration, characterized in that an effective amount of the above-described compound of formula (1), an acid addition salt thereof, or a hydrate of the compound or the acid addition salt is administered to a subject in need thereof.

DESCRIPTION OF PREFERRED EMBODIMENTS

The above-described compound of formula (1) is a known compound. It is described, for example, in Japanese Patent Application Laid-Open (kokai) No. 3-2144 (corresponding to EP541798B). Although this publication states that the compound may be advantageously used as a cerebral protecting agent for ameliorating or preventing the progress of cerebral hemorrhage, cerebral infarction, subarachnoidal hemorrhage, transient cerebral ischemic attack, cerebrovascular disorder, or the like, the publication does not suggest as to whether the present compound has the action to inhibit cell adhesion and cellular infiltration.

In formula (1), examples of the halogen atoms represented by $R^1$ through $R^6$ include fluorine, chlorine, bromine, and iodine. Of these, fluorine, chlorine, and iodine are preferred. Examples of lower alkyl groups include $C_1$-$C_6$ alkyl groups such as methyl, ethyl, n-propyl, isopropyl, n-butyl, i-butyl, t-butyl, pentyl, and hexyl. Particularly, methyl, ethyl, n-propyl, and isopropyl are preferred. Examples of lower alkoxy groups include $C_1$-$C_6$ alkoxy groups such as methoxy, ethoxy, propoxy, butoxy, pentyloxy, and hexyloxy. Of these, methoxy, ethoxy, and propoxy are preferred.

The compound of formula (1) may be prepared by the method described for example in Japanese Patent Application Laid-Open (kokai) No. 3-2144 (corresponding to EP541798B), and preferably by the method (1) described in that publication.

In the present invention, acid addition salts of formula (1) compound may also be used. Acid addition salts can be prepared by a routine method. As examples of the acids which are used for preparing the acid addition salts, there are inorganic acids such as sulfuric acid, hydrochloric acid, nitric acid, phosphoric acid, and hydrobromic acid; and organic acids such as acetic acid, lactic acid, succinic acid, tartaric acid, malic acid, maleic acid, citric acid, fumaric acid, methanesulfonic acid, and toluenesufonic acid. Also, the hydrates which are used in the present invention may be those of formula (1) compound or of the acid addition salts of formula (1) compound.

As will be described hereinlater, the compound of formula (1) has excellent cell adhesion inhibitory action and cellular infiltration inhibitory action. Examples of pathological conditions which are attributed to cell adhesion or cellular infiltration include allergic diseases, asthma, inflammations, rheumatism, arterioscrelosis, and cancerous metastasis. Compounds of formula (1) are useful for the prevention and treatment of these pathological conditions.

The pharmaceuticals according to the present invention contain compounds of formula (1), acid addition salts thereof, or hydrates thereof as their active ingredients. These active ingredients are used singly or in combination with pharmaceutically acceptable excipients, binders, carriers, diluents, etc. and formulated into tablets, capsules, granules, injections, or suppositories. These formulations can be prepared by known methods. For example, in order to prepare formulations for oral administration, compounds of formula (1) are blended together with excipients such as starch, mannitol, and lactose; binders such as carboxymethylcellulose-Na and hydroxypropylcellulose; disintegrators such as crystalline cellulose and carboxymethylcellulose-Ca; lubricants such as talc and magnesium stearate; and fluidity improvers such as light silicic acid anhydride.

The dose of the pharmaceutical of the present invention varies depending on the patient's body weight, age, sex, conditions, etc. In general, a dose from 0.1 to 1,000 mg/day in terms of the formula (1) compound is preferred for an adult, which is administered in a single daily dose, or the total daily dose may be administered in divided doses of two or three times daily.

EXAMPLES

The present invention will be explained in more detail by the following examples, which should not be construed as limiting the present invention.

PREPARATION EXAMPLE 1

Preparation of N,N'-bis-((Z)-5-(3,4,5-trimethoxyphenyl)-4-pentenyl)homopiperazine In a round-bottomed flask fitted with a calcium chloride tube, dimethylformamide (20 ml), (Z)-5-(3,4,5-trimethoxyphenyl)- 4-pentenyl bromide (1.2 g), homopiperazine (0.171 g), potassium carbonate (0.514 g), and potassium iodide (0.754 g) were placed. The mixture was stirred for 2 hours in a 100° C. bath.

After completion of reaction, ethyl acetate was added, the insoluble matter was filtered using celite, and the filtrate was concentrated under reduced pressure. A saturated aqueous sodium hydrogencarbonate solution was added to the residue, and the mixture was extracted with ethyl acetate, followed by washing with saturated brine, and drying. The solvent was evaporated and the residue was purified by silica gel column chromatography (chloroform:methanol=50:1), to thereby obtain 0.745 g of the target compound as a pale yellow oily material.

This free base was treated by a routine method using 2N HCl/dioxane so as to give 0.63 g of a dihydrochloride of the target compound.

Dihydrochloride

IR(KBr): 3409, 2931, 2566, 1577, 1502, 1456cm$^{-1}$.

NMR (CD$_3$OD) δ: 1.76–2.20 (4H, m, 2 X CH=CHCH$_2$CH$_2$), 2.20–2.64(6H, m, 2 X CH=CHCH$_2$,& NCH$_2$CH$_2$CH$_2$N), 3.00–3.96(12H, m, NCH$_2$CH$_2$CH$_2$N, NCH$_2$CH$_2$N & 2 X CH=CHCH$_2$CH$_2$CH$_2$), 3.78(6H, s, 2 X CH$_3$O), 3.95 (12H, s, 4 X CH$_3$O), 5.86 (2H, m, 2 X CH=CHCH$_2$), 6.49 (2H, d, J=10 Hz, 2 X CH=CHCH$_2$), 6.55(4H, s, aromatic H).

PREPARATION EXAMPLE 2

Preparation of N,N'-bis-((E)-5-(3,4,5-trimethoxyphenyl)-4-pentenyl)homopiperazine In a round-bottomed flask fitted with a calcium chloride tube, dimethylformamide (20 ml), (E)-5-(3,4,5-trimethoxyphenyl)-4-pentenyl bromide (1.37 g), homopiperazine (0.195 g), potassium carbonate (0.600 g), and potassium iodide (0.862 g) were placed. The mixture was stirred for 2 hours in a 100° C. bath.

After completion of reaction, ethyl acetate was added, the insoluble matter was filtered using celite, and the filtrate was concentrated under reduced pressure. A saturated aqueous sodium hydrogencarbonate solution was added to the residue, and the mixture was extracted with ethyl acetate, followed by washing with saturated brine, and drying. The solvent was evaporated and the residue was purified by silica gel column chromatography (chloroform:methanol=50:1), to thereby obtain 0.619 g of the target compound as a pale yellow oily material.

This free base was treated by a routine method using 2N HCl/dioxane so as to give 0.534 g of a dihydrochloride of the target compound.

Dihydrochloride

Melting point: 103° C.

IR(KBr): 3410, 2931, 2568, 1580, 1502, 1451, 1416 cm$^{-1}$.

NMR(CD$_3$OD) δ: 1.80–2.22(4H, m, 2 X CH=CHCH$_2$CH$_2$), 2.22–2.60(6H, m, 2 X CH=CHCH$_2$ & NCH$_2$CH$_2$CH$_2$N), 3.16–4.00(12H, m, NCH$_2$CH$_2$CH$_2$N, NCH$_2$CH$_2$N & 2 X CH=CHCH$_2$CH$_2$CH$_2$), 3.80(6H, s, 2 X CH$_3$O), 3.88

(12H, s, 4 X CH₃O), 6.32(2H, dt, J=15.6, 5.2 Hz, 2 X CH=CHCH₂), 6.53(2H, d, J=15.6 Hz, 2 X CH=CHCH₂), 6.76(4H, s, aromatic H).

PREPARATION EXAMPLE 3

Preparation of N,N'-bis-((E)-3-(2-methoxyphenyl)-2-propenyl)piperazine

2-Methoxy-cinnamylalcohol (1.44 g) was chlorinated using thionylchloride. Subsequently, reaction with piperazine and other treatments were performed as described in Preparation Example 2, to thereby obtain 314 mg of a salt as colorless prisms.

Melting point: 193°–194° C.

NMR(CDCl₃) δ: 2.45–2.75

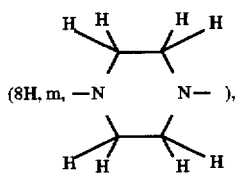

(8H, m, —N  N— ), 3.20

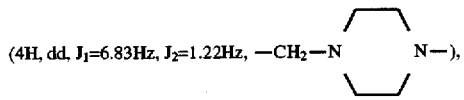

(4H, dd, J₁=6.83Hz, J₂=1.22Hz, —CH₂—N  N—), 3.84(6H, s, 2 x CH₃O—), 6.24–6.35 (2H, m, 2 x CH=CH—CH₂), 6.82–6.94(6H, m, 2 x CH=CH—CH₂ & aromatic H), 7.18–7.26(2H, m, aromatic H), 7.44(2H, dd, J₁=7.57 Hz, J₂=1.7 Hz, aromatic H).

PREPARATION EXAMPLE 4

Preparation of N,N'-bis-((E)-3-(2-methoxyphenyl)-2-propenyl)homopiperazine

Using 2-methoxy-cinnamylalcohol, a procedure similar to that described in Preparation Example 3 was repeated, so as to perform reactions with thionylchloride then with homopiperazine as well as other treatments, to thereby obtain a free base of the target compound as a pale yellow amorphous.

Melting point: 181°–182° C.

NMR(CDCl₃) δ: 1.85–2.00

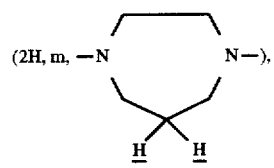

(2H, m, —N  N—), 2.82–2.87

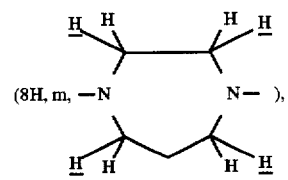

(8H, m, —N  N— ), 3.35(4H, dd, J₁=6.84 Hz, J₂=0.98 Hz, 2 x CH=CH—CH₂), 3.84(6H, s, 2 x CH₃O—), 6.25–6.36(2H, m, 2 x CH=CH—CH₂), 6.82–6.94(6H, m, 2 x CH=CH—CH₂ & aromatic) 7.18–7.26(2H, m, aromatic H), 7.45 (2H, dd, J₁=7.57 Hz, J₂=1.7 Hz, aromatic H).

PREPARATION EXAMPLE 5

Preparation of N,N'-bis-((E)-5-(4-methoxyphenyl)-4-pentenyl)piperazine

Using (E)-5-(4-methoxyphenyl)-4-pentenyl bromide (383 mg), reactions and treatment were performed in a manner similar to that described in Preparation Example 2, to thereby obtain 198 mg of a free base of the target compound as colorless needles.

Melting point: 124°–126° C.

IR(KBr): 2939, 2923, 1607, 1510, 1245cm⁻¹.

NMR(CDCl₃) δ: 1.67(4H, quint, 2 x N—CH₂CH₂CH₂), 2.21(4H, q, 2 x NCH₂CH₂CH₂), 2.39(4H, t, 2 x N—CH₂ ), 2.51(8H,m, 2 X N—CH₂CH₂N), 3.80(6H, S, 2 x OCH₃), 6.06(2H, dt, J=6.84, 15.86 Hz, 2 X CH₂—CH=CH—), 6.33(2H, d, J=15.86 Hz, 2 x CH₂—CH=CH—), 6.83(4H, d, J=8.79 Hz, aromatic H), 7.26(4H, d, J=8.79 Hz, aromatic H).

The present invention will next be described in detail taking several typical compounds of the present invention as examples for demonstrating the cell adhesion inhibitory action, cellular infiltration inhibitory action, and other biological actions including antiallergic action, antiasthmatic action, antiinflammatory action, antirheumatic action, and antiarteriosclerotic action of the compounds.

TEST COMPOUND 1

N,N'-bis-((Z)-5-(3,4,5-trimethoxyphenyl)-4-pentenyl) homopiperazine.2HCl (Preparation Example 1)

TEST COMPOUND 2

N,N'-bis-((E)-5-(3,4,5-trimethoxyphenyl)-4-pentenyl) homopiperazine.2HCl (Preparation Example 2)

TEST COMPOUND 3

N,N'-bis-((E)-3-(2-methoxyphenyl)-2-propenyl) piperazine.2HCl (Preparation Example 3)

TEST COMPOUND 4

N,N'-bis-((E)-5-(4-methoxyphenyl)-4-pentenyl) piperazine (Preparation Example 5)

EXAMPLE 1

Cell Adhesion Inhibitory Effect

The test was performed with reference to a method described by Ross et al (J. Biol. Chem., 267, 8537–8543 (1992)). Briefly, endothelial cells derived from the human umbilical code vein (HUVEC) were cultured in a 48-well plate until they became confluent. Subsequently, IL-1β or TNFα was added. Five hours after the addition, U937 cells which are derived from human monocytes/histiocytes and FITC-labeled with PKH2 (Dainippon Seiyaku) were added to each well in an amount of 3×10⁵ cells per well. After being allowed to stand for 45 minutes at room temperature, U937 cells which had not been adhered to were washed off, and the remaining cells were lysed using 1% Triton X-100. Fluorescent intensity was measured (Exi. 494 nm, Emi. 504 nm). The HUVEC cells were cultured in EGM-UV (Kurabo Industries Ltd.), and U937 cells were cultured in RPMI1640 plus 10% FCS. Each test drug (compound) was added to HUVEC simultaneously with the addition of IL-1β or TNFα, or to U937 cells 24 hours before the cell adhesion test, to thereby study the effect of the compound. The inhibitory activity was determined by the following equation:

(the number of drug-free U937 cells adhered to drug-free endothelial cells that have been stimulated with IL-1β or TNFα)—(the number of drug-free U937 cells adhered to drug-free endothelial cells that have not been stimulated with IL-1β or TNFα)=100%

The results are shown in Table 1.

TABLE 1

Cell Adhesion Inhibitory Action

| Test Compound | Cell Adhesion ($IC_{50}$: μM) | |
| --- | --- | --- |
| (No.) | IL-1β Stimulation | TNFα Stimulation |
| 1 | 9.7 | 8.0 |
| 2 | 9.0 | 9.5 |
| 3 | 3.4 | 12.9 |
| 4 | 11.1 | 9.4 |

EXAMPLE 2

Inhibition of Eosinocyte Infiltration in a Guinea Pig Asthma Model

In accordance with a method described by Terashi (Allergy, 37, 980–991 (1988)), groups of Hartley male guinea pigs, each group consisting of 4–7 animals (body weight: about 300 g), were exposed to chicken egg albumin (10 mg/ml) by way of inhalation using a ultrasonic nebulizer for 10 minutes a day for successive 9 days, to thereby create a sensitized state of the animals. From the following day, test compound 2 was intraperitoneally administered to each animal for successive 6 days (10 or 30 mg/kg). On day 7, metopyrone (10 mg/kg) and chlorphenylamine (10 mg/kg) were intraperitoneally administered to each animal. Thirty minutes later, each animal was exposed to chicken egg albumin (10 mg/ml) for 10 minutes by way of inhalation. In addition, 2 hours thereafter, test compound 2 was intraperitoneally administered to each animal. Twenty-four hours later, each animal was exsanguinated to death, and its trachea was removed. The trachea was fixed with formalin and embedded in paraffin, so as to prepare thin slice samples. The samples were subjected to luna staining, and eosinocytes that infiltrated were counted. The results are shown in Table 2.

TABLE 2

Eosinocyte Infiltration Inhibitory Action
in a Guinea Pig Asthma Model

| Group | Infiltration of trachea by eosinocytes (cells/mm) |
| --- | --- |
| No sensitization (blank) | 67.7 ± 7.2 |
| Control | 204.5 ± 15.3 |
| Test Compound 2 (10 mg/kg) | 171.0 ± 6.5 (p <0.05) |
| Test Compound 2 (30 mg/kg) | 122.2 ± 7.0 (p <0.01) |

EXAMPLE 3

Lymphocyte Infiltration Inhibitory Action in Mouse Contact Dermatitis

In accordance with a method described by Asherson et al. (Immunology, 15, 405–416 (1968)), action of the compound on lymphocyte infiltration in mouse contact dermatitis was investigated. Groups of ddy male mice that had been sensitized with picryl chloride, each group consisting of 10 animals (body weight: 28–32 g), were provided for the test. Test compound 2 was intraperitoneally administered to each animal for successive 6 days before induction took place (1 or 10 mg/kg). A 1% solution of picryl chloride-olive oil (0.02 ml) was applied to an ear of each animal. Twenty-four hours later, both ears were punched (7 mmφ), to thereby compute the difference in weight. The ears were then embedded in paraffin, frozen, and cut in a vertical direction with respect to the ear face to prepare thin slices each having a thickness of 4 μm. CD3 positive cells were immunostained and counted. The results are shown in Table 3.

TABLE 3

Lymphocyte Infiltration Inhibitory Action
in a Mouse Contact Dermatitis

| Group | Ear weight (mg/7 mmφ) | Count of CD3 positive cells (cells/mm) |
| --- | --- | --- |
| Control | 4.9 ± 0.7 | 10.8 ± 1.3 |
| Test Compound 2 (1 mg/kg) | 4.5 ± 0.8 | 7.8 ± 0.4 (p <0.05) |
| Test Compound 2 (10 mg/kg) | 2.9 ± 0.6 (p <0.05) | 4.2 ± 0.7 (p <0.01) |

EXAMPLE 4

Leukocyte Infiltration Inhibitory Action in Rat Carrageenin Pleurisy

In accordance with a method described by Kikuchi et al. (Japan J. Pharmacol., 39, 467–473 (1985)), action of the compound on leukocyte infiltration in rat carrageenin pleurisy was investigated. Groups of SD male mice, each group consisting of 6 animals (7 weeks old), were provided for the test. Test compound 2 was intraperitoneally administered to each animal for successive 2 days (10 or 30 mg/kg). Two hours after the final administration, a 2% (w/v) carrageenin solution (0.1 ml) was intrathoracically administered. Sixteen hours later, each animal was exsanguinated to death, and pleural fluid was collected. The volume of the collected pleural fluid was measured, and cells that infiltrated and present in the pleural fluid were counted. The results are shown in Table 4.

TABLE 4

Leukocyte Infiltration Inhibitory Action
in a Rat Carrageenin Pleurisy

| Group | Pleural fluid volume (ml) | Count of infiltrated cells ($\times 10^8$) |
| --- | --- | --- |
| Control | 3.3 ± 0.3 | 2.37 ± 0.06 |
| Test Compound 2 (10 mg/kg) | 2.5 ± 0.3 | 1.97 ± 0.05 |
| Test Compound 2 (30 mg/kg) | 2.5 ± 0.3 (p <0.05) | 1.68 ± 0.22 (p <0.01) |

EXAMPLE 5

Action of Compound on Mouse Type II Collagen Arthritis

The test was performed in accordance with a method described by Ranges et al. (J. Exp. Med., 162, 1105–1110 (1985)). To each of DBA/1 male mice (6–7 weeks old), 100 μg of type II collagen from bovine suspended in Freund's complete adjuvant was subcutaneously injected at the root of its tail. Twenty one days later, the mice was given a booster injection in a similar manner. The drug was intraperitoneally administered to each mouse once every day starting from 2 days prior to the booster injection until 7 days after the booster injection (a total of 10 times). The severity of arthritis was evaluated by measuring the thickness of the front foot pads. In addition, antibody titers (IgG+IgM) against type II collagen in serum were determined by ELISA. The results are shown in Table 5.

TABLE 5

Action on Mouse Type II Collagen Arthritis

| Group | Thickness of front foot pad ($\times 10^{-2}$ mm) After 30 days | Antibody titer against collagen After 33 days* |
|---|---|---|
| No sensitization (blank) | 361.0 ± 4.2 | 0 ± 0.00 |
| Control | 421.3 ± 13.1 | 1.00 ± 0.13 |
| Test Compound 2 (30 mg/kg) | 384.8 ± 6.9 ($p <0.05$) | 0.43 ± 0.10 ($p <0.01$) |

*IgG + IgM (percentage with respect to the value of control)

Specific formulation examples will next be described below.

EXAMPLE 6 (CAPSULES)

| | |
|---|---|
| N,N'-bis-((E)-5-(3,4,5-trimethoxyphenyl)-4-pentenyl)homopiperazine.2HCl | 30 mg |
| Microcrystalline cellulose | 30 mg |
| Lactose | 57 mg |
| Magnesium stearate | 3 mg |
| Total amount | 120 mg |

The above ingredients were mixed by a known method, and then placed in a gelatin capsule to obtain a capsulated agent.

EXAMPLE 7 (TABLETS)

| | |
|---|---|
| N,N'-bis-((E)-5-(3,4,5-trimethoxyphenyl)-4-pentenyl)homopiperazine.2HCl | 30 mg |
| Starch | 44 mg |
| Starch powder (for pastes) | 5.6 mg |
| Magnesium stearate | 0.4 mg |
| Carboxymethylcellulose-Ca | 20 mg |
| Total amount | 120 mg |

The above ingredients were mixed by a known method to obtain a tablet.

EXAMPLE 8 (INJECTION LIQUID)

N,N'-bis-((E)-5-(3,4,5-trimethoxyphenyl)-4-pentenyl)homopiperazine.2HCl (100 mg) and NaCl (900 mg) were dissolved in about 80 ml of distilled water for injection, and to the resultant solution was added distilled water for injection so as to make the total amount 100 ml. The obtained solution was aseptically filtered and dispensed into 10 light-shielded ampules. The ampules were sealed to thereby give an aseptic injection liquid.

As described above, compound of formula (1) exhibits excellent cell adhesion inhibitory action and cellular infiltration inhibitory action with suppressed toxicity. Therefore, the compound is useful as an antiphlogistic, antiasthmatic agent, antiallergic agent, antirheumatic agent, antiarteriosclerotic agent, and cancerous metastasis inhibitory agent.

What is claimed is:

1. A method for inhibiting cell adhesion and/or cellular infiltration, which comprises interacting cells with a compound of the following formula (1):

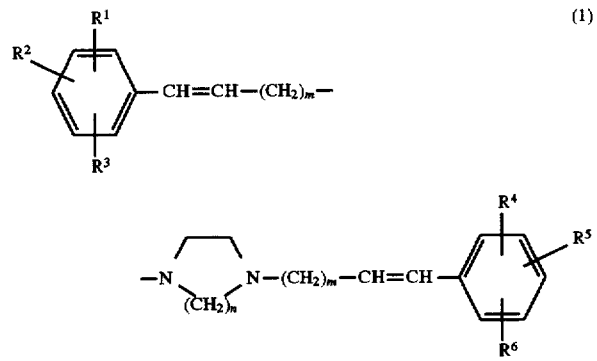

wherein each of $R^1$, $R^2$, $R^3$, $R^4$, $R^5$ and $R^6$, which are identical to or different from each other, represents a hydrogen atom, a halogen atom, a hydroxyl group, a lower alkyl group, or a lower alkoxy group, m represents a number of 1 from 3 inclusive, and n represents 2 or 3; an acid addition salt thereof; or a hydrate of the compound or the acid addition salt.

2. A preventive or therapeutic method for pathological conditions selected from the group consisting of allergic diseases, asthma, inflammations, rheumatism and arteriosclerosis, which comprises administering to a subject in need thereof an effective amount of a compound of the following formula (1):

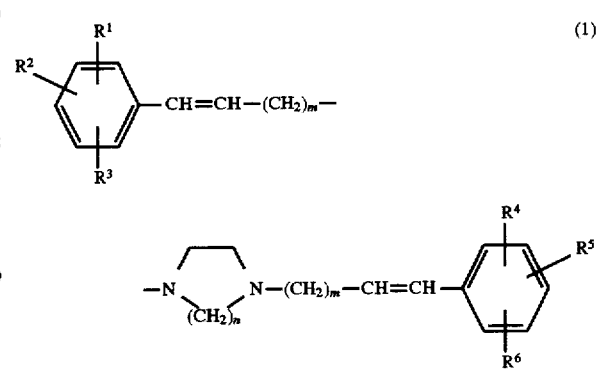

wherein each of $R^1$, $R^2$, $R^3$, $R^4$, $R^5$, and $R^6$, which are identical to or different from each other, represents a hydrogen atom, a halogen atom, a hydroxyl group, a lower alkyl group, or a lower alkoxy group, m represents a number of 1 to 3 inclusive, and n represents 2 or 3; an acid addition salt thereof; or a hydrate of the compound or the acid addition salt.

* * * * *